United States Patent
Mundis et al.

(10) Patent No.: US 9,339,306 B2
(45) Date of Patent: May 17, 2016

(54) ADJUSTABLE AXIAL SPINAL ROD CONNECTOR

(71) Applicant: K2M, Leesburg, VA (US)

(72) Inventors: Gregory Mundis, San Diego, CA (US); Burt Yaszay, San Diego, CA (US)

(73) Assignee: K2M, Inc., Leesburg, VA (US)

( * ) Notice: Subject to any disclaimer, the term of this patent is extended or adjusted under 35 U.S.C. 154(b) by 135 days.

(21) Appl. No.: 14/013,641

(22) Filed: Aug. 29, 2013

(65) Prior Publication Data

US 2014/0066989 A1    Mar. 6, 2014

Related U.S. Application Data

(60) Provisional application No. 61/694,317, filed on Aug. 29, 2012.

(51) Int. Cl.
*A61B 17/70* (2006.01)

(52) U.S. Cl.
CPC ........... *A61B 17/705* (2013.01); *A61B 17/7083* (2013.01)

(58) Field of Classification Search
CPC .......................... A61B 17/705; A61B 17/7083
USPC ......... 606/246, 256, 258, 259, 260, 261, 264, 606/270, 278, 279
See application file for complete search history.

(56) References Cited

U.S. PATENT DOCUMENTS

| | | | |
|---|---|---|---|
| 4,404,967 A * | 9/1983 | Bacal et al. | 606/276 |
| 4,433,677 A * | 2/1984 | Ulrich et al. | 606/250 |
| 4,628,919 A * | 12/1986 | Clyburn | 606/55 |
| 6,110,173 A * | 8/2000 | Thomas, Jr. | 606/252 |
| 6,241,730 B1 | 6/2001 | Alby | |
| 7,175,622 B2 | 2/2007 | Farris | |
| 7,909,852 B2 | 3/2011 | Boomer et al. | |
| 7,931,676 B2 * | 4/2011 | Veldman et al. | 606/261 |
| 7,935,134 B2 | 5/2011 | Reglos et al. | |
| 7,942,908 B2 | 5/2011 | Sacher et al. | |
| 8,097,022 B2 | 1/2012 | Marik | |
| 8,147,519 B2 | 4/2012 | Wilcox | |
| 8,372,121 B2 | 2/2013 | Capote et al. | |
| 8,382,803 B2 | 2/2013 | Schmocker | |
| 8,475,499 B2 | 7/2013 | Cournoyer et al. | |
| 2006/0229611 A1 | 10/2006 | Avery et al. | |
| 2008/0027436 A1* | 1/2008 | Cournoyer et al. | 606/61 |
| 2008/0195100 A1* | 8/2008 | Capote et al. | 606/71 |

(Continued)

OTHER PUBLICATIONS

U.S. Appl. No. 14/013,680, filed Aug. 29, 2013, Akbarnia et al.

*Primary Examiner* — Pedro Philogene
*Assistant Examiner* — David C Comstock
(74) *Attorney, Agent, or Firm* — Carter, Deluca, Farrell & Schmidt, LLP (57) ABSTRACT

An axial spinal rod connector includes a central connector and first and second portions. The first and second portions are each integrally formed with the central connector to define a longitudinal axis. Each of the first and second portions includes an outer end portion and a set screw. The outer end portion defines a passage about the longitudinal axis and defines a blind hole orthogonal to the longitudinal axis. The blind hole extends into the passage. The passage is sized and configured to slidably receive a spinal rod. The set screw is sized and configured to engage the blind hole. The set screw at lease partially interfering with the passage when engaged with the blind hole to fix a spinal rod relative to the spinal rod connector.

18 Claims, 11 Drawing Sheets

(56) References Cited

U.S. PATENT DOCUMENTS

| | | |
|---|---|---|
| 2009/0163953 A1 | 6/2009 | Biedermann et al. |
| 2010/0036423 A1 | 2/2010 | Hayes et al. |
| 2010/0086378 A1* | 4/2010 | Lin .............................. 411/436 |
| 2011/0054536 A1* | 3/2011 | Elsebaie et al. ............... 606/264 |
| 2013/0066375 A1 | 3/2013 | Biedermann et al. |

* cited by examiner

ADJUSTABLE AXIAL SPINAL ROD CONNECTOR

CROSS-REFERENCE TO OTHER APPLICATIONS

This application claims priority to and the benefit of U.S. Provisional Application Ser. No. 61/694,317 filed Aug. 29, 2012, the disclosure of which is hereby incorporated by reference in its entirety.

BACKGROUND

1. Technical Field

The present disclosure relates to a device for use in orthopedic surgeries and, more specifically, to axial spinal rod connectors that are axially adjustable.

2. Discussion of Related Art

The human spinal column is a highly complex structure. It includes twenty-four discrete bones, known as vertebrae, coupled sequentially to one another to house and protect critical elements of the nervous system. The cervical portion of the spine, which includes the neck of the spine up to the base of the skull, includes the first seven vertebrae.

Disease, the effects of aging, or physical trauma resulting in damage to the spine has been treated in many instances by fixation or stabilization of the affected vertebra. A wide variety of spinal fixation apparatuses have been employed in surgical procedures for correcting spinal injuries and the effects of spinal diseases. Many of these apparatuses commonly use a pair of longitudinal rods running in a relatively parallel relationship to each other. Additional fixation methods are also employed that mate with the spinal rod to provide additional points of fixation. These include, but are not limited to, head to head connectors, rod to rod transverse connectors, hooks and axial rod to rod connectors.

Axial spinal rod to rod connectors are often used in subsequent surgeries when there is existing hardware already implanted in the patient. The axial spinal rod connector is used to continue the spinal rod construct from the original hardware to the new hardware that is implanted. The axial spinal rod connector provides support for the new hardware and helps to orient it appropriately with the existing hardware. In addition, an axial spinal rod connector may be used as a bridge between sections of hardware if there are two separate, non-adjacent regions that require instrumentation. Sometimes the upper thoracic region requires instrumentation as well as the lumbar region and the axial spinal rod connector may be used to connect the spinal rod from these two regions. The axial spinal rod connectors are made in various lengths, preferably 20-90 mm in length, and also may accept various spinal rod diameters, shapes and materials, for example if a smaller 4.5 mm spinal rod is used in the thoracic region and a 5.5 mm spinal rod is used in the lumbar region, the axial spinal rod connector can accommodate both of these sized spinal rods and connect with both spinal rods.

A need exists for an axial spinal rod connector that is longitudinally adjustable for discrete and precise movement of the spinal rod in set increments which affords control over the axial tension on the spinal rod between spinal constructs.

SUMMARY

In aspects of the present disclosure, an axial spinal rod connector includes a central connector, a first portion, and a second portion. Each of the first and second portions is integrally formed with the central connector and defines a longitudinal axis. The longitudinal axis of the first and second portions may be aligned. Each of the first and second portions including an outer end portion and a set screw. Each outer end portion defines a passage about the longitudinal axis and a blind hole orthogonal to the longitudinal axis. The blind hole extends into the passage. The passage is sized and configured to slidably receive a spinal rod. The set screw sized and configured to engage the blind hole. The set screw at least partially interferes with the passage when it is engaged with the blind hole to fix a position of a spinal rod relative to the spinal rod connector.

In aspects of the present disclosure, the central portion defines a central passage such that the passages of the first and second portions and the central portion define a lumen. In embodiments, the lumen has a uniform size and shape along the length thereof.

In aspects of the present disclosure, the passage is a cylindrical stepped hole that has a first diameter in the outer end portion and a central diameter smaller than the first diameter at the central connector. The passage defines a stop at the transition from the first diameter to the central diameter. The stop and the central connector may define a gap therebetween.

In aspects of the present disclosure, each outer end portion further includes a stop inserted through the sidewalls of the respective first and second portion. The stop interfering with the passage of the respective portion to define a gap between the stop and the central portion. In aspects of the present disclosure, the passage is generally rectangular shaped and has an arcuate bottom.

In aspects of the present disclosure, the first and second portions each define a slot through a top surface of the respective portion between the central connector and the outer end portion. The slot may extend through the bottom surface of the respective portion. In aspects of the present disclosure, the central connector includes opposing notches on an outer surface thereof. The notches are sized and configured to receive a forceps.

In aspects of the present disclosure, the passage in the first portion defines a first diameter and the passage of the second portion defines a second diameter different from the first diameter. The central connector may define a central passage having a central diameter smaller than the first and second diameters.

In aspects of the present disclosure, a method for adjusting an axial spinal rod connector includes positioning a spinal rod connector over an end of a first spinal rod, adjusting the axial spinal rod connector until a desired length of the first spinal rod is received within the passage of the first portion, inserting a first set screw into the blind hole of the first portion, and tightening the first set screw to fix the first spinal rod to the first portion. In embodiments, adjusting the axial spinal rod connector includes viewing the end of the first spinal rod through a slot in a top surface of the first portion. In some embodiments adjusting the axial spinal rod connector includes engaging a blind hole of a first portion with a distal end of a first handle of a pusher instrument and inserting a numb of a distal end of a second handle of the pusher instrument into the slot of the first portion and manipulating the first and second handles of the pusher instrument such that the nub engages the end of the first spinal rod until a desired length of the first spinal rod is received within the passage of the first portion. In particular embodiments, the top surface of the first portion includes markings and adjusting the axial spinal rod connector further includes aligning the end of the first spinal rod with one of the markings corresponding to the desired length.

In aspects of the present disclosure, a kit includes an axial spinal rod connector and a pusher instrument.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closer to the clinician and the term "distal" will refer to the portion of the device or component thereof that is farther from the clinician. In addition, the term "cephalad" is used in this application to indicate a direction toward a patient's head, whereas the term "caudad" indicates a direction toward the patient's feet. Further still, for the purposes of this application, the term "medial" indicates a direction toward a side of the body of the patient, i.e., away from the middle of the body of the patient. The term "posterior" indicates a direction toward the patient's back, and the term "anterior" indicates a direction toward the patient's front. Additionally, in the drawings and in the description that follows, terms such as front, rear, upper, lower, top, bottom, and similar directional terms are used simply for convenience of description and are not intended to limit the disclosure.

Figure 1:
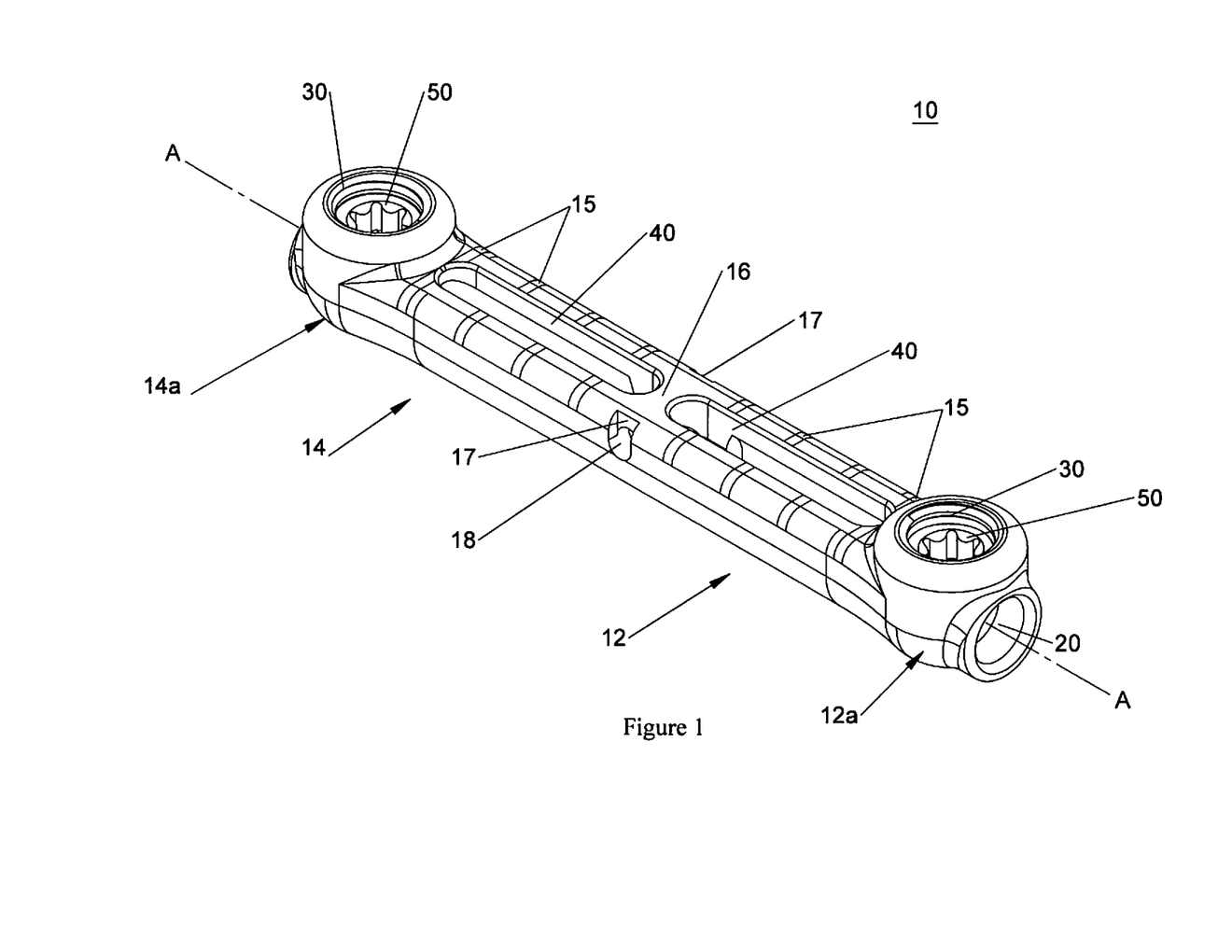
FIG. 1 is a perspective view of an exemplary embodiment of an adjustable axial spinal rod connector in accordance with the present disclosure.

With reference to FIG. 1, an adjustable axial spinal rod connector 10 is provided in accordance with the present disclosure including first and second portions 12, 14 integrally joined by a central connector 16. First and second portions 12, 14 define a longitudinal axis A-A. First and second portions 12, 14 are similar to one another with like elements represented with like labels.

Figure 2:
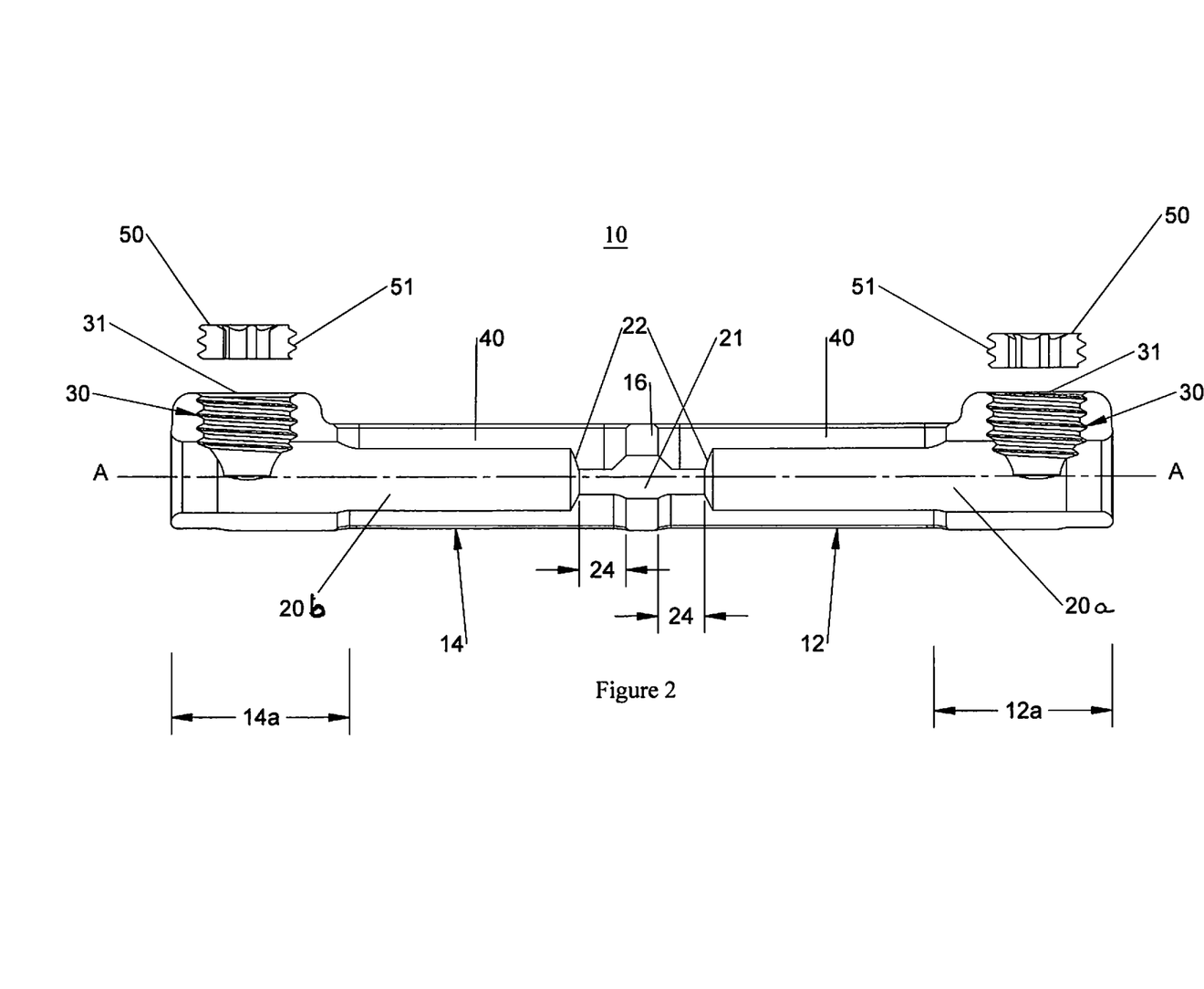
FIG. 2 is a side cross-sectional view of the rod connector of FIG. 1 taken along the longitudinal axis with the set screws removed from the blind holes.

With additional reference to FIG. 2, first and second portions 12, 14 have outer end portions 12a, 14a respectively. Passages 20a, 20b are defined about the longitudinal axis extending from respective outer end portions 12a, 14a towards central connector 16. As shown, passages 20a, 20b are generally cylindrical. It is envisioned that passages 20a, 20b have shapes other than cylindrical. It is also envisioned that one of passages 20a, 20b can have a first shape in the first portion 12 and the other of passages 20a, 20b can have a second shape different from the first shape in the second portion 14. In some embodiments, central connector 16 includes a central passage 21 such that passages 20a, 20b and central passage 21 form stepped through-holes. In some embodiments, central passage 21 has a diameter less than the diameter of both passages 20a, 20b. The steps defined between passages 20a, 20b and central passage 21 form stops 22 near central connector 16. Stop 22 defines a gap 24 with central portion 16 as shown in FIG. 2. In particular embodiments, passages 20a, 20b and central passage 21 define a channel or lumen 20 (FIG. 1). Lumen 20 may have a constant size and shape from outer end portion 12a of first portion 12 to outer end portion 14a of second portion 14 extending through central connector 16.

Outer end portions 12a, 14a each define a blind hole 30 extending through the top surface of first and second portions 12, 14 into passage 20a, 20b. Each blind hole 30 is orthogonal to longitudinal axis A-A. Blind holes 30 include threads 31 that are configured to cooperate with threads 51 of set screws 50. Set screws 50 have sufficient length to engage threads 31 and interfere with passage 20a, 20b. First and second portions 12 and 14 can each define a slot 40 between outer end portions 12a, 14a and central connector 16. Slot 40 extends through the top surface of each portion 12, 14 and into passage 20a, 20b. In embodiments, slot 40 is a through-slot extending through the top and bottom surfaces of each of first and second portions 12, 14. The top surface of first and second portions 12, 14 can have markings 15 spaced at predefined distances along slot 40.

Central connector 16 can include notches 17. In some embodiments, a through hole 18 is defined between notches 17 near the base of each notch 17. Notches 17 are configured to receive a forceps (not shown) as described in detail below.

Figure 3:
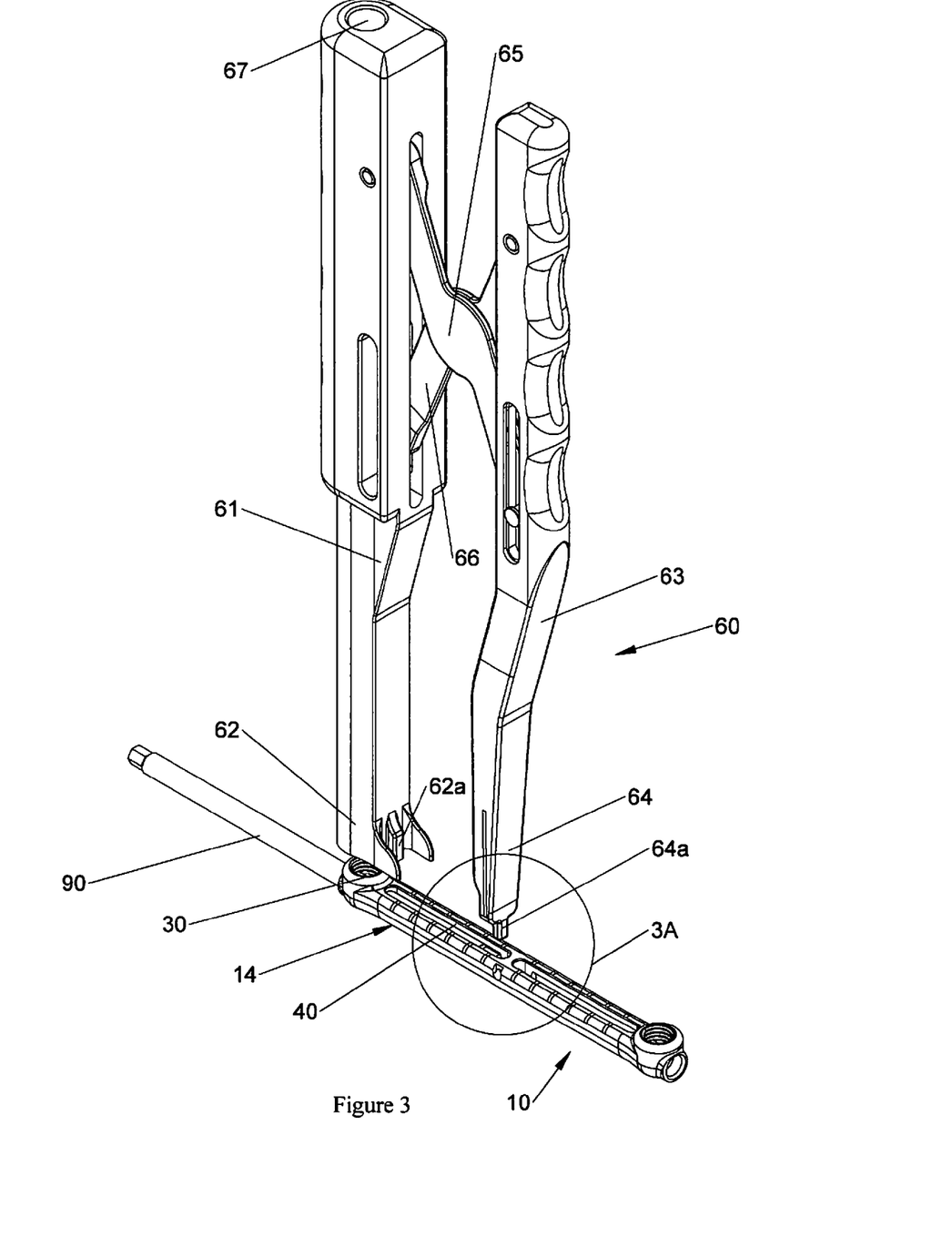
FIG. 3 is perspective view of a system for adjusting the rod connector of FIG. 1 including a pusher instrument.

Referring to FIG. 3, a pusher instrument 60 is provided in accordance with the present disclosure including first and second handles 61, 63 joined by first and second arms 65, 66. Each handle 61, 63 has a distal end 62, 64 respectively. Distal end 62 of first handle 61 is configured to engage an outer end 12a, 14a of rod connector 10. In embodiments, distal end 62 of first handle 61 includes a finger 62a that engages an end of slot 40 and distal end 64 of second handle 63 includes a nub 64a insertable into slot 40. First handle 61 defines a screw passage 67 sized and configured to permit and/or guide set screw 50 into blind hole 30 when pusher instrument 60 is engaged with blind hole 30 as described below.

Figure 5:
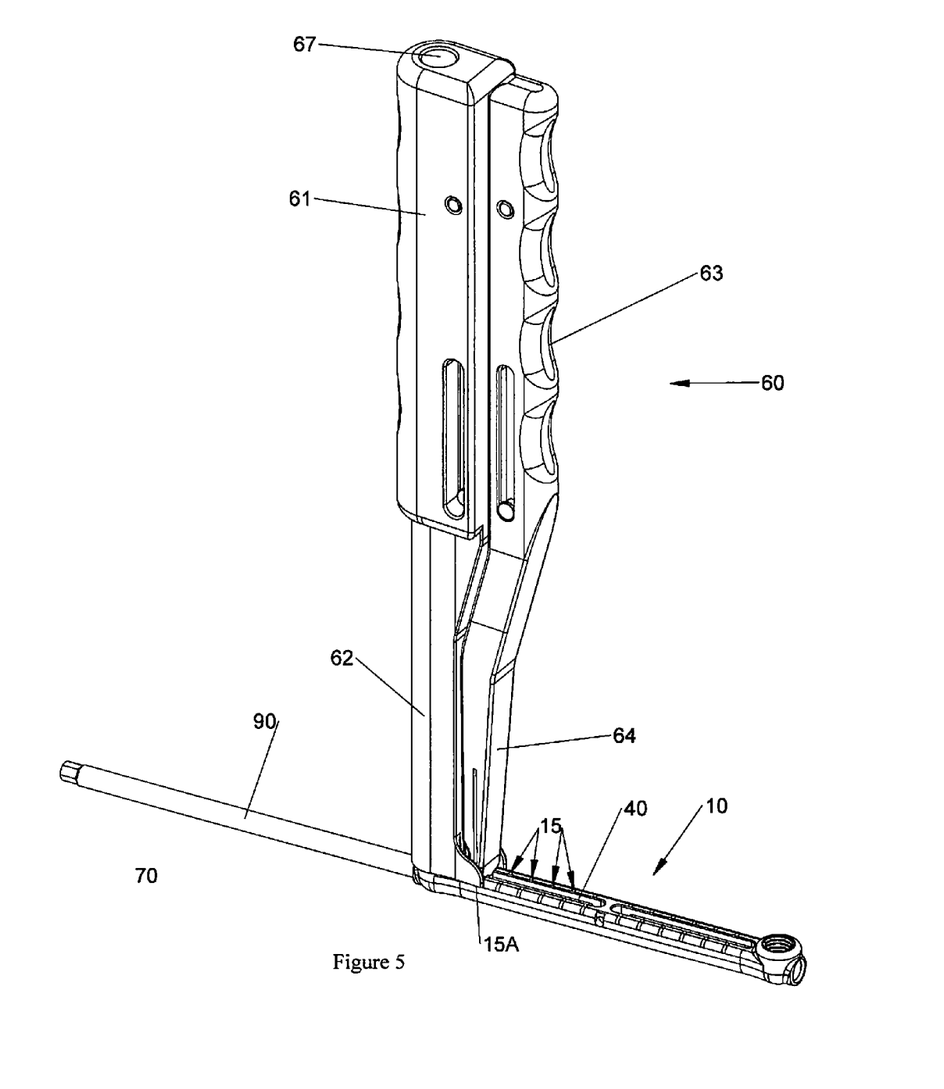
FIG. 5 is a perspective view of the system of FIG. 3 with the pusher instrument engaged with the rod connector in a closed condition.

Referring to FIGS. 3 and 5, first and second handles 61, 63 have a spaced-apart position (FIG. 3) and a closed position (FIG. 5). First and second handles 61, 63 are configured to maintain first and second handles substantially parallel to one another as first and second handles 61, 63 transition between the spaced-apart and closed positions.

Figure 3A:
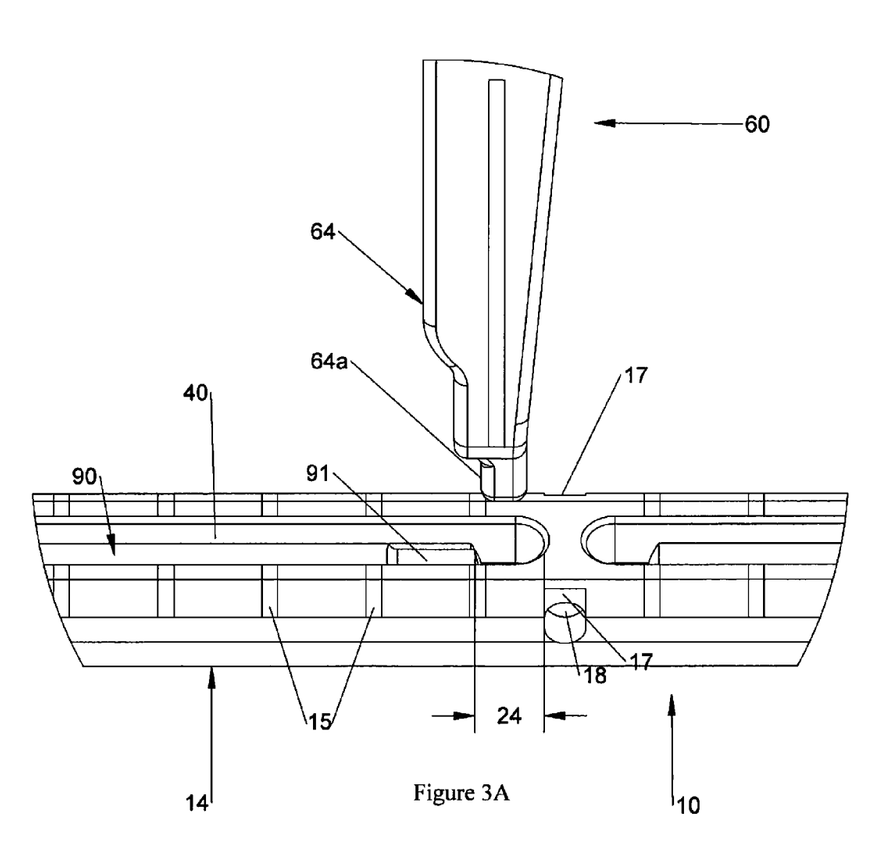
FIG. 3A is an enlargement of the detail area shown in FIG. 3.
Figure 4:
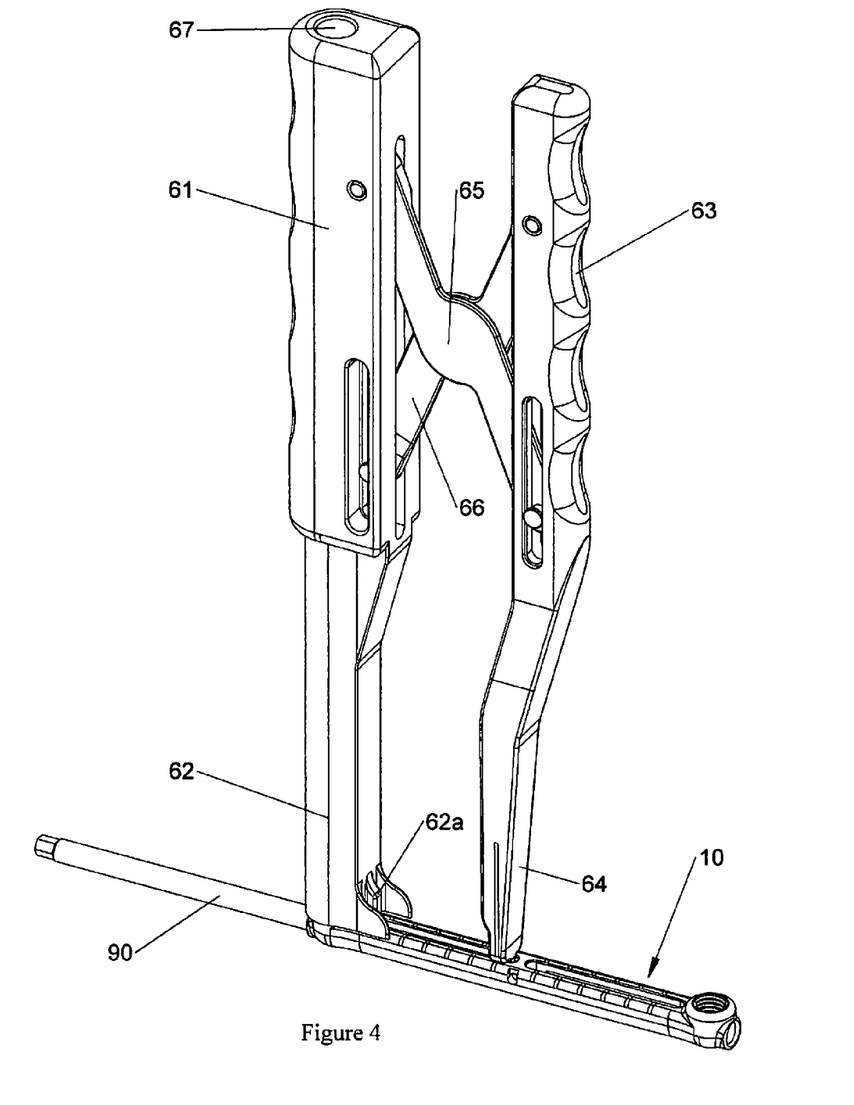
FIG. 4 is a perspective view of the system of FIG. 3 with the pusher instrument engaged with the rod connector in a spaced-apart position.

Referring to FIGS. 3-5, rod connector 10 is coupled to a spinal rod 90 in accordance with the present disclosure. Pusher instrument 60 can be used to adjust spinal rod 90 relative to rod connector 10 as rod connector 10 is coupled to spinal rod 90. An end 91 of spinal rod 90 is inserted into passage 20b of second portion 14 as shown in FIG. 3. End 91 is visible through slot 40 and is positioned near but not past central connector 16 as shown in FIG. 3A. A forceps (not shown) can be used to position rod connector 10 over spinal rod 90. The forceps can engage notches 17 and/or through hole 18 to position rod connector 10. Markings 15 can be used to provide indicia of the length of spinal rod 90 disposed within passage 20b.

Referring to FIG. 4, distal end 62 of pusher instrument 60 is positioned over blind hole 30 of second portion 14 with pusher instrument 60 in the space-apart condition. Finger 62a can engage an end of slot 40 of second portion 14 near end portion 14a. Distal end 64 of pusher instrument 60 is inserted into slot 40 of second portion 14 between end 91 of spinal rod 90 and central connector 16. First and second handles 61, 63 of pusher instrument are manipulated to move first and second handles 61, 63 towards the closed condition to adjust the length of spinal rod 90 disposed within passage 20b. As first and second handles 61, 63 are moved towards the closed condition, finger 62a engages blind hole to fix first handle 61 relative to connector 10 and nub 64a of second handle 63 engages end 91 of spinal rod 90 to adjust the position of end 91 or length of spinal rod 90 within passage 20b by causing relative movement between spinal rod 90 and connector 10 such that the length of spinal rod 90 disposed in passage 20b is reduced as handles 61, 63 are moved towards the closed condition. First and second handles 61, 63 are manipulated until end 91 of spinal rod 90 is at a desired position within passage 20b corresponding to a desired length of spinal rod 90 disposed within passage 20b. Markings 15 can be used as indicia of the desired length and/or desired position. End 91 of spinal rod 90 is viewable through slot 40 and may be aligned with a desired marking 15a of markings 15 on the top surface of second portion 14 corresponding to the desired position. When end 91 of spinal rod 90 is at the desired position, a set screw 50 (FIG. 1) is inserted into blind hole 30 of second portion 14. Set screw 50 can be inserted through screw hole 67 of pusher instrument 60. Set screw 50 engages the portion of spinal rod 90 adjacent blind hole 30. A screw tool (not shown) can be inserted through screw hole 67 to engage set screw 50 with spinal rod 90. When set screw 50 is tightened such that spinal rod 90 is fixed relative to rod connector 10, pusher instrument 60 is removed. It is envisioned that set screw 50 is configured to engage spinal rods of varying diameter and shapes to fix the spinal rods to rod connector 10.

Set screw 50 can be inserted into blind hole 30 to partially engage spinal rod 90 before first and second handles 61, 63 of pusher instrument 60 are manipulated to adjust spinal rod 90. The partial engagement of set screw 50 with spinal rod 90 provides some resistance to the adjustment of spinal rod 90.

It is also envisioned that set spinal rod 90 can be inserted and fixed within passage 20b without adjusting the position of spinal rod 90 relative to rod connector 10 with pusher instrument 60.

The above process is repeated relative to a second spinal rod (not shown) inserted through passage 20a of first portion 12. An end of the second spinal rod may be inserted through passage 20a of first portion 12 before set screw 50 is tightened to fix the second spinal rod relative to rod connector 10. Pusher instrument 60 can be used to adjust the position of the second spinal rod relative to rod connector 10 in the manner described above with respect to spinal rod 90. The desired length and/or desired position of each spinal rod may correspond to a desired tension between spinal rod 90 and the second spinal rod.

Figure 6:
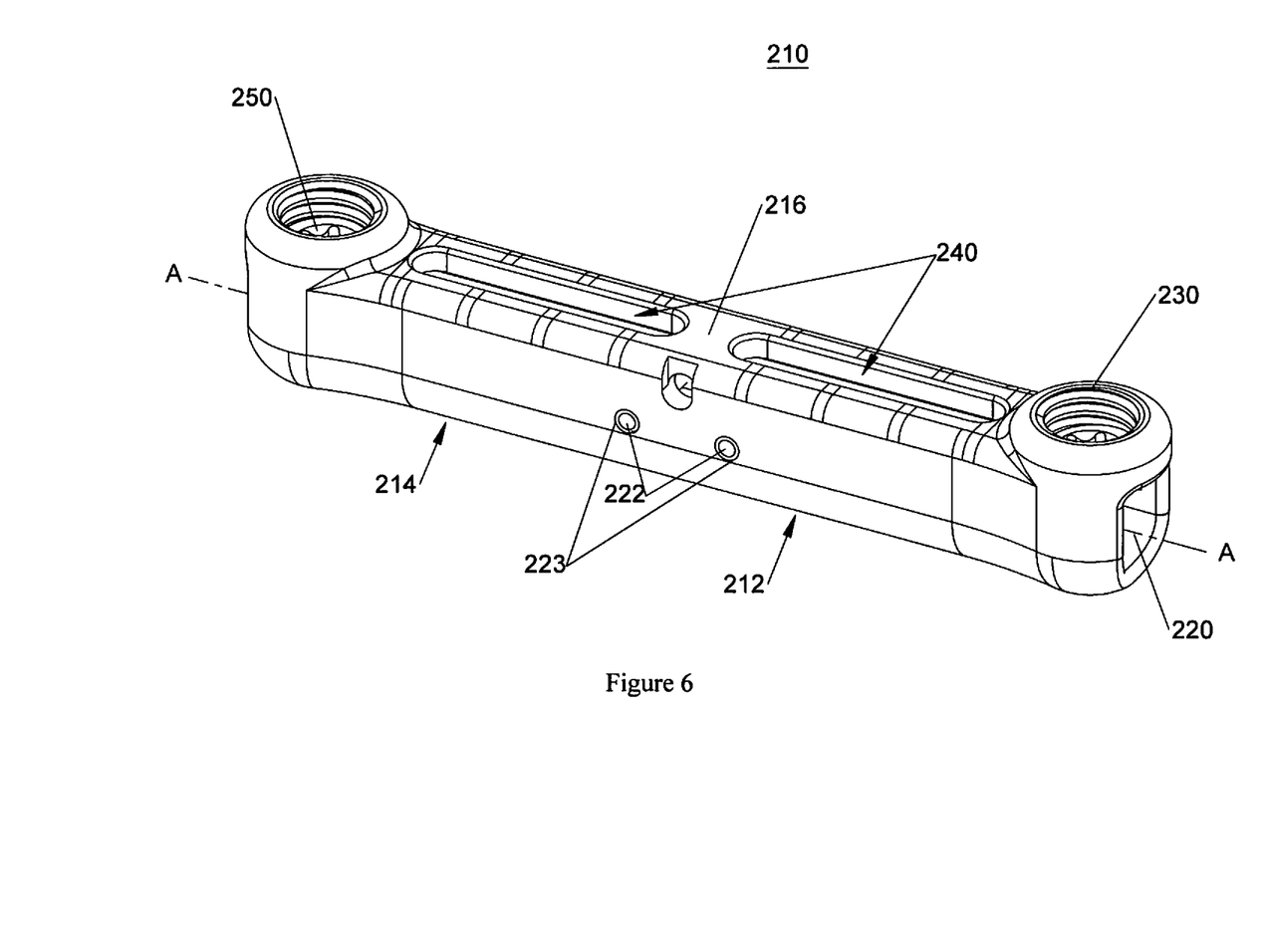
FIG. 6 is a perspective view of another exemplary embodiment of an adjustable axial spinal rod connector in accordance with the present disclosure.
Figure 7:
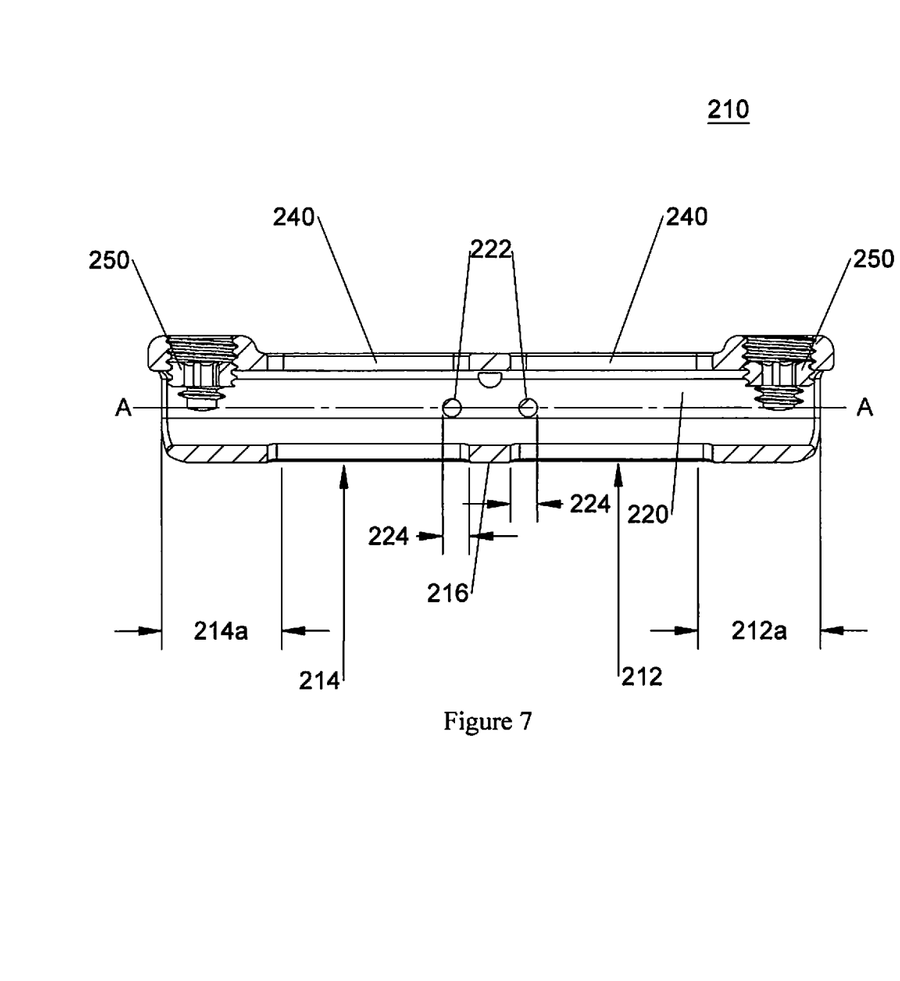
FIG. 7 is a side cross-sectional view of the rod connector of FIG. 6 taken along the longitudinal axis.
Figure 7A:
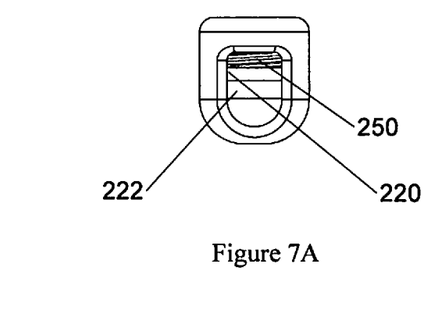
FIG. 7A is a front view of the rod connector of FIG. 6.

Referring to FIGS. 6-7A, another exemplary embodiment of an adjustable axial spinal rod connector 210 in accordance with the present disclosure includes first and second portions 212, 214 integrally joined with a central connector 216. First and second portions 212, 214 of rod connector 200 are substantially similar to first and second portions 12, 14 of rod connector 10, as such only the differences will be described in detail below.

A through passage 220 is defined through first portion 212, second portion 214, and central connector 216. Through passage 220 has a substantially rectangular shape sized and configured to receive a spinal rod (not shown) having a similar shape. The bottom of through passage 220 can be arcuate as shown in FIG. 7A. Rod connector 210 can include stops 222 positioned within passage 220 near central connector 216. In embodiments, stops 222 are pins inserted in openings 223 through sidewalls of first and second portions 212, 214 orthogonal to longitudinal axis A-A. In embodiments, the sidewalls of first and second portions 212, 214 include a plurality of openings 223 each of the plurality of openings 223 corresponding to a desired length of a spinal rod (FIG. 3) within passage 220. Stops 222 may define a gap 224 with central connector 216. Gap 224 may be sized and configured to be larger than nub 64a of distal end 64 of pusher instrument 60 such that distal end 64 can be inserted through slot 240 between an end of a spinal rod (not shown) when the end of the spinal rod is inserted within passage 220 abutting stop 222.

Figure 8:
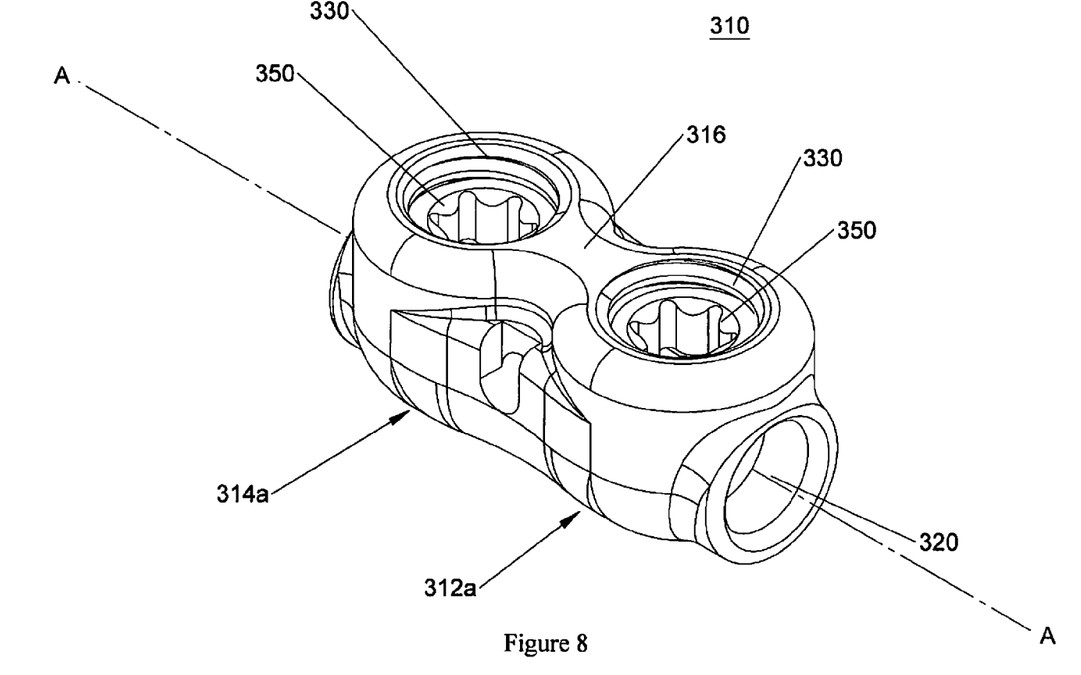
FIG. 8 is a perspective view of yet another exemplary embodiment of an adjustable axial spinal rod connector in accordance with the present disclosure.

Referring to FIG. 8, yet another exemplary embodiment of an adjustable axial spinal rod connector 310 in accordance with the present disclosure includes outer end portions 312a, 314a integrally joined by a central connector 316. Outer end portions 312a, 314a of rod connector 310 are substantially similar to outer end portions 12a, 14a of rod connector 10, as such only the differences will be discussed in detail below.

First and second end portions 312a, 314a define a through passage 320 sized and configured to slidably receive spinal rods (not shown) as described above with respect to rod connector 10. Set screws 330 are inserted through blind holes 330 to engage the spinal rods and are configured to fix the spinal rods relative to rod connector 310.

Figure 9:
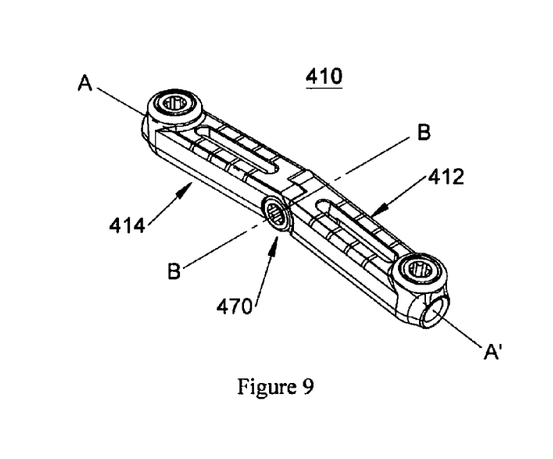
FIG. 9 is a perspective view of still another exemplary embodiment of an adjustable axial spinal rod connector in accordance with the present disclosure including an adjustable connector assembly.
Figure 10:
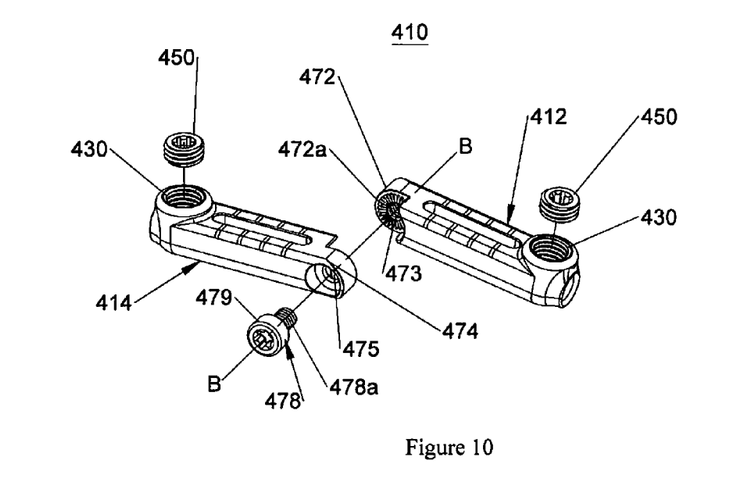
FIG. 10 is an exploded view of the components of the rod connector of FIG. 9.
Figure 11:
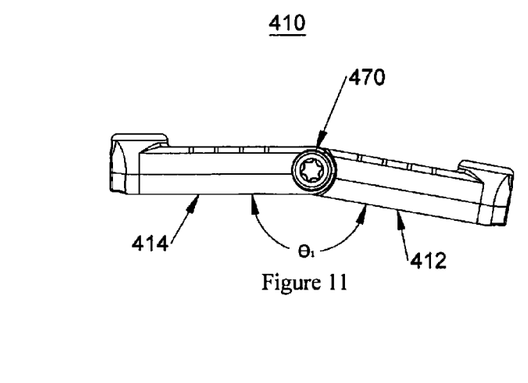
FIG. 11 is a side view of the rod connector of FIG. 9.

Referring to FIGS. 9-11, still another exemplary embodiment of an adjustable axial spinal rod connector 410 is provided in accordance with the present disclosure including first and second portions 412, 414 joined by an articulating connector assembly 470. First and second portions 412, 414 of rod connector 410 are substantially similar to first and second portion 12, 14 of rod connector 10 described above, as such only the differences will be described in detail below.

First portion 412 defines a longitudinal A'-A' and second portion 414 defines a longitudinal axis A-A. Articulating connector assembly 470 defines an axis B-B that passes through first and second portions 412, 414 perpendicular to sidewalls thereof intersecting and orthogonal to longitudinal axes A-A and A'-A'. Articulating connector assembly 470 is configured to articulate first and second portions 412, 414 in a fixed plane relative to one another about longitudinal axis B-B. Such an articulating connector assembly is disclosed in co-owned and co-pending U.S. Patent Publication No. 2014/0066990, the content of which is incorporated in its entirety. Each of first and second portions 412, 414 include a connecting flange 472, 474 positioned at an inner end 412b, 414b of first and second portions 412, 414, respectively. Each flange 472, 474 defines a through connecting hole 473, 475 sized and configured to receive a connector 478. A surface 472a of flange 472 can include radial features. As shown in FIG. 10, connecting hole 473 is threaded and configured to cooperate with threads 478a of connector 478. Connection hole 475 includes a recess 476 sized and configured to receive connector 478 such that a head 479 of connector 478 is flush with or disposed within the side wall of second portion 414. First and second portions 412, 414 each include a blind hole 430 and a set screw 450 insertable within blind hole 430.

In use, spinal rods (not shown) are inserted through passages 420 and fixed relative to first and second portions 412, 414 in the manner describe above with respect to connector 10. Flanges 472, 474 of first and second portions 412, 414 are aligned such that connecting holes 473, 475 are aligned. An angle $\theta_1$ can be defined between the bottom surfaces of first and second portions 412, 414. It will be appreciated that during installation angle $\theta_1$ may initially be about 0° or 180° and is adjustable in either direction, i.e., clockwise or counter-clockwise about axis B-B. In one embodiment, angle $\theta_1$ can be in the range of about 45° to about 315°. In another embodiment, angle $\theta_1$ can be in a range of about 180° to about 90° or 270° depending on the relative rotation of the first and second portions 412, 414. In a further embodiment, angle $\theta_1$ can be in a range of about 170° to about 90°. When angle $\theta_1$ is at a desired angle, connector 478 is tightened to angularly fix the first and second portions 412, 414 relative to one another. Radial features 472a can engage radial features on a surface (not shown) of flange 474 to angularly fix first and section portions 412, 414. It will be appreciated that rod connector 410 can be used to connect spinal rods which are not axially aligned.

Figures 12, 13, 14:
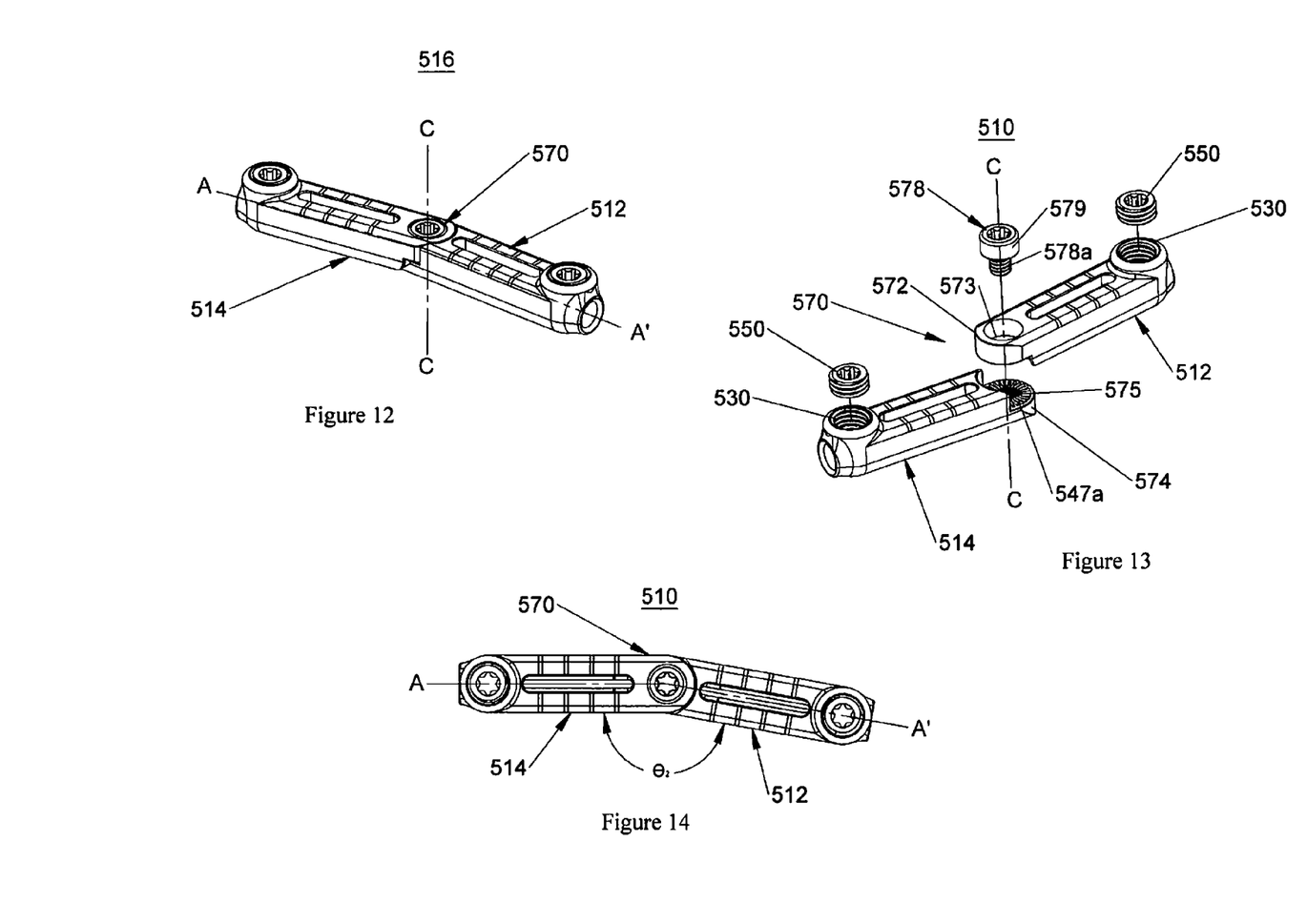
FIG. 12 is a perspective view of still yet another exemplary embodiment of an adjustable axial spinal rod connector in accordance with the present disclosure including an adjustable connector assembly.
FIG. 13 is an exploded view of the components of the rod connector of FIG. 12.
FIG. 14 is a top view of the rod connector of FIG. 12.

Referring to FIGS. 12-14, still yet another exemplary embodiment of an adjustable axial spinal rod connector 510 is provided in accordance with the present disclosure including first and second portions 512, 514 joined by an articulating connector assembly 570. First and second portions 512, 514 and articulating connector assembly 570 of rod connector 510 are substantially similar to first and second portion 412, 414 and articulating connector assembly 470 of rod connector 410 described above, as such only the differences will be described in detail below.

First portion 512 defines a longitudinal A'-A' and second portion 514 defines a longitudinal axis A-A. Connector assembly 570 defines an axis C-C that passes through first and second portions 512, 514 perpendicular to the top and bottom surfaces thereof intersecting and orthogonal to longitudinal axes A-A and A'-A'. Articulating connector assembly 570 is configured to articulate first and second portions 512, 514 in a fixed plane relative to one another about longitudinal axis C-C. Such an articulating connector assembly is disclosed in co-owned and co-pending U.S. Patent Publication No. 2014/0066990, the content of which is incorporated in its entirety. Each of first and second portions 512, 514 include a connecting flange 572, 574 positioned at an inner end 512b, 514b of first and second portions 512, 514, respectively. Each flange 572, 574 defines a through connecting hole 573, 575 sized and configured to receive a connector 578. A surface 574a of flange 574 includes radial features. As shown in FIG. 10, connecting hole 573 is threaded and configured to cooperate with threads 578a of connector 578. Connection hole 575 includes a recess 576 sized and configured to receive connector 578 such that a head 579 of connector 578 is flush with or disposed within the top surface of second portion 514. First and second portions 512, 514 each include a blind hole 530 and a set screw 550 insertable within blind hole 530.

In use, spinal rods (not shown) are inserted through passages 520 and fixed relative to first and second portions 512, 514 in the manner describe above with respect to connector 10. Flanges 572, 574 of first and second portions 512, 514 are aligned such that connecting holes 573, 575 are aligned. An angle $\theta_2$ can be defined between the sidewalls of first and second portions 512, 514. Angle $\theta_2$ can be in the range of about 45° to about 315°. It will be appreciated that during installation angle $\theta_2$ may initially be about 0° or 180° and is adjustable in either direction, i.e., clockwise or counter-clockwise about axis C-C. When angle $\theta_2$ is at a desired angle, connector 578 is tightened to angularly fix the first and second portions 512, 514 relative to one another. In one embodiment, angle $\theta_2$ can be in the range of about 45° to about 315°. In another embodiment, angle $\theta_2$ can be in a range of about 180° to about 90° or 270° depending on the relative rotation of the first and second portions 512, 514. In a further embodiment, angle $\theta_2$ can be in a range of about 170° to about 90°. Radial features 574a can engage radial features on a surface (not shown) of flange 572 to angularly fix first and section portions 512, 514. It will be appreciated that rod connector 510 can be used to connect spinal rods which are not axially aligned.

It is also envisioned that an adjustable spinal rod connector (not shown) can be provided in accordance with the present disclosure including first and second portions integrally joined by a central connector. The first and second portions defining a fixed angle θ1 between the bottom surfaces of the first and second portions and/or defining a fixed angle θ2 between the sidewalls of the first and second portions. Such an adjustable axial spinal rod connector is disclosed in co-owned and co-pending U.S. Patent Publication No. 2014/0066990 the content of which is incorporated in its entirety.

In an aspect of the present disclosure, a kit is provided in accordance with the present disclosure including an adjustable axial spinal rod connector and a pusher instrument disposed within a sealed package. The rod connector and the pusher instrument can be sterilized before being sealed in the package. Any of the above adjustable axial spinal rod connectors 10, 110, 210, 310, 410, and 510 and pusher instrument 60 described above can be provided as part of the kit.

In aspects of the present disclosure, any or all of the screws, e.g., screws 50, 250, 350, 450, 478, 550, and 578, further include one or more locking mechanisms configured such that, when the screw is inserted into hole, the locking mechanism maintains the screw within the hole. The locking mechanism may include, for example, a locking ring positionable in the hole for retaining the screw, a lip formed in the hole with the screw made of a harder material than the hole such that a thread on the screw, e.g., a second screw thread disposed about the screw head, locks to the lip upon engagement of the screw with the lip, or any other suitable locking mechanism.

In aspects of the present disclosure, the adjustable axial spinal rod connectors described above may be constructed of a variety of biocompatible materials, e.g., stainless steel, cobalt chrome, PEEK, titanium, titanium alloys, etc.

In aspects of the present disclosure, the spinal rods described above may be made in various diameters and various shapes and may be constructed of a variety of biocompatible materials, e.g., stainless steel, cobalt chrome, PEEK, titanium, titanium alloys, etc.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. An axial spinal rod connector comprising:
a central connector defining a central passage having a central diameter; and
first and second portions each integrally formed with the central connector to define a longitudinal axis, each of the first and second portions including:
an outer end portion defining a passage about the longitudinal axis and defining a blind hole orthogonal to the longitudinal axis, the blind hole extending into the passage, the passage sized and configured to slidably receive a spinal rod, the passage having a diameter larger than the central diameter; and
a set screw sized and configured to engage the blind hole, the set screw at least partially interfering with the passage when engaged with the blind hole to fix a position of the spinal rod relative to the spinal rod connector, the blind holes configured to receive a portion of a pusher instrument to adjust a length of a spinal rod received within the passage.

2. The spinal rod connector of claim 1, wherein the longitudinal axis of the first portion is aligned with the longitudinal axis of the second portion.

3. The spinal rod connector of claim 2, wherein the passages of the first and second portions and the central passage define a lumen.

4. The spinal rod connector of claim 1, wherein the passage is a cylindrical stepped hole having a first diameter adjacent the blind hole and a second diameter smaller than the first diameter adjacent the central connector, the passage defining a stop at the transition from the first diameter to the second diameter.

5. The spinal rod connector of claim 4, wherein the stop and the central connector define a gap therebetween.

6. The spinal rod connector of claim 1, wherein each outer end portion further includes a stop inserted through sidewalls and the passage of the respective first and second portions, the stop interfering with the passage of the respective portion to define a gap between the stop and the central portion.

7. The spinal rod connector of claim 4, wherein the second diameter is smaller than the central diameter.

8. The spinal rod connector of claim 1, wherein each of the first and second portions further defines a slot through a top surface thereof between the central connector and the outer end portion.

9. The spinal rod connector of claim 8, wherein the slot extends through the bottom surface.

10. The spinal rod connector of claim 1, wherein the central connector includes opposing notches on an outer surface thereof, the notches sized and configured to receive a forceps.

11. The spinal rod connector of claim 1, wherein the passage in the first portion defines a first diameter and the passage of the second portion defines a second diameter different from the first diameter.

12. The spinal rod connector of claim 1, wherein the central connector is adapted to prevent a spinal rod from passing between the first and second portions.

13. A method for adjusting an axial spinal rod connector, the method comprising:
positioning the spinal rod connector over an end of a first spinal rod, the spinal rod connector including:
a central connector defining a central passage having a central diameter; and
first and second portions each integrally formed with the central connector to define a longitudinal axis, each of the first and second portions including an outer end portion, the outer end portion of each of the first and second portions defining a passage about the longitudinal axis and defining a blind hole orthogonal to the longitudinal axis, the blind hole extending into the passage, the passage of the first portion receiving the end of the first spinal rod, the passage having a diameter larger than the central diameter, each of the first and second portions defining a slot through a top surface in communication with the passage;
adjusting the axial spinal rod connector until a desired length of the first spinal rod is received within the passage of the first portion by engaging the blind hole of the first portion with a distal end of a first handle of a pusher instrument and inserting a nub of a distal end of a second handle of the pusher instrument into the slot of the first portion;
inserting a first set screw into the blind hole of the first portion; and
tightening the first set screw to fix the first spinal rod to the first portion.

14. The method of claim 13, wherein adjusting the axial spinal rod connector further includes viewing the end of the first spinal rod through the slot.

15. The method of claim 14, wherein a top surface of the first portion includes markings and adjusting the axial spinal rod connector further includes aligning the end of the first spinal rod with one of the markings corresponding to the desired length.

16. The method of claim 13, wherein adjusting the axial spinal rod connector further includes:
manipulating the first and second handles of the pusher instrument such that the nub engages the end of the first spinal rod until a desired length of the first spinal rod is received within the passage of the first portion.

17. A kit comprising:
an axial spinal rod connector including:
a central connector defining a central passage having a central diameter; and
first and second portions each integrally formed with the central connector and each defining a longitudinal axis, each of the first and second portions including:
an outer end portion defining a passage about the longitudinal axis and defining a blind hole orthogonal to the longitudinal axis, the blind hole extending into the passage, the passage sized and configured to slidably receive a spinal rod, the passage having a diameter larger than the central diameter; and
a set screw sized and configured to engage the blind hole, the set screw at least partially interfering with the passage when engaged with the blind hole to fix a position of a spinal rod relative to the spinal rod connector; and
a pusher instrument including a first handle and a second handle, a distal end of the first handle configured to engage the blind hole of a respective one of the first or second portions and a distal end of the second handle configured to be received within a slot of a one of the first or second portions to adjust a length of a spinal rod within one of the passages of the axial spinal rod connector.

18. An axial spinal rod connector comprising:

a central connector defining a central passage having a central diameter;

a first portion integrally formed with the central connector to define a longitudinal axis, the first portion including a first outer end portion defining a first passage about the longitudinal axis and defining a first blind hole orthogonal to the longitudinal axis, the first blind hole extending into the first passage, the first passage having a diameter larger than the central diameter, the first blind hole configured to receive a portion of a pusher instrument to adjust a length of a spinal rod received within the first passage; and a second portion integrally formed with the central connector including a second outer end portion defining a second passage about the longitudinal axis and defining a second blind hole orthogonal to the longitudinal axis, the second blind hole extending into the second passage, the second passage having a diameter larger than the central diameter.

* * * * *